(12) United States Patent
Boutignon et al.

(10) Patent No.: US 8,206,688 B2
(45) Date of Patent: Jun. 26, 2012

(54) FOAM-FORMING COMPOSITION

(75) Inventors: Francois Jean-Louis Jerome Boutignon, Clermont-Ferrand (FR); Jean-Marc Aiache, Clermont-Ferrand (FR); Thomas Jean Henri Barres, Chamalieres (FR); Florian Tapissier, Clermont-Ferrand (FR)

(73) Assignee: Disphar International B.V., Hengelo (NL)

( * ) Notice: Subject to any disclaimer, the term of this patent is extended or adjusted under 35 U.S.C. 154(b) by 392 days.

(21) Appl. No.: 12/161,102

(22) PCT Filed: Jan. 12, 2007

(86) PCT No.: PCT/EP2007/000271
§ 371 (c)(1),
(2), (4) Date: Mar. 16, 2010

(87) PCT Pub. No.: WO2007/082698
PCT Pub. Date: Jul. 26, 2007

(65) Prior Publication Data
US 2010/0166672 A1    Jul. 1, 2010

Related U.S. Application Data

(60) Provisional application No. 60/761,779, filed on Jan. 25, 2006.

(30) Foreign Application Priority Data

Jan. 19, 2006    (EP) ..................................... 06100572

(51) Int. Cl.
*A61K 9/12*       (2006.01)
*A61K 31/56*      (2006.01)

(52) U.S. Cl. .............. 424/45; 424/436; 521/72; 521/78; 521/98

(58) Field of Classification Search ................... 424/45, 424/47, 61, 400
See application file for complete search history.

(56) References Cited

U.S. PATENT DOCUMENTS

| 5,061,491 | A | * | 10/1991 | Deryabin ...................... 424/730 |
| 5,089,252 | A | * | 2/1992 | Grollier et al. .................. 424/47 |
| 5,725,872 | A |   | 3/1998 | Stamm et al. |
| 5,972,310 | A |   | 10/1999 | Sachetto et al. |
| 2005/0069499 | A1 |   | 3/2005 | Arkin et al. |
| 2005/0271598 | A1 |   | 12/2005 | Friedman et al. |
| 2006/0140984 | A1 | * | 6/2006 | Tamarkin et al. ............. 424/400 |

OTHER PUBLICATIONS

International Search Report for Application No. PCT/EP2007/000271, dated May 3, 2007.

* cited by examiner

*Primary Examiner* — Walter Webb
(74) *Attorney, Agent, or Firm* — Nelson Mullins Riley & Scarborough LLP; John Resek; Pankaj N. Desai

(57) ABSTRACT

The present invention relates to a novel foam-forming composition suitable for rectal administration of locally-acting pharmaceutically active ingredients, and the product adapted to administer said foam-forming composition. Also, the present invention relates to a method for its preparation. According to the present invention a foam-forming composition is provided which exhibits a high expansion ratio and at the same time conferring optimal appearance of the formed foam to allow sufficient contact time of the active to the target site in the intestine in order to obtain optimal local effect. The composition according to the present inventions provides superior properties for the treatment of rectal diseases.

23 Claims, No Drawings

FOAM-FORMING COMPOSITION

RELATED APPLICATIONS

This application is a 35 U.S.C. §371 filing of International Application Number PCT/EP2007/000271 which was filed on Jan. 12, 2007, which claims priority to U.S. Provisional Application No. 60/761,799, which was filed on Jan. 25, 2006 and European Patent Application EP 06 100 572.4, which was filed on Jan. 19, 2006. The entire contents of the aforementioned applications are hereby incorporated herein by reference.

FIELD OF THE INVENTION

The present invention relates to a novel foam-forming composition suitable for rectal administration of prednisolone and a product adapted to administer said foam-forming composition. Also, the present invention relates to a method for its preparation.

BACKGROUND OF THE INVENTION

Left-sided (distal) ulcerative colitis and ulcerative proctitis are disease subtypes of ulcerative colitis with multiple treatment options. In addition to oral formulations used in patients with extensive colitis or pancolitis, those with disease limited to the distal 60 cm from the anal verge also have the option of topical rectal therapies with aminosalicylates or glucocorticoid formulations [R. D. Cohen et al. The American Journal of Gastroenterology; Vol. 95, No. 5, 2000; p. 1263]. Suitable dosage forms for rectal delivery include suppositories, foams and liquid enemas, which differ with respect to their physiochemical properties and potential for proximal spread. A randomized prospective comparison of foams versus liquid enemas reported that patients preferred the foam because of greater comfort, ease of retention and minimal interference with their daily routine. The disadvantage of using foams instead of liquid enemas is the decreased proximal spread of the foam. Whereas liquid enemas have been shown to extend reliably as far as the splenic flexure, the foam can only reach the proximal sigmoid colon [J. K. Marshall of al. The American Journal of Gastroenterology; vol. 95, No. 7, 2000: p. 1628]. Especially when the rectal treatment involves the use of the sparingly absorbed and hence locally-acting prednisolone metasulphobenzoate, the efficacy of the therapy is dependent upon direct contact of this active ingredient with the inflamed mucosa. Hence it is important that a highly expanded volume of the foam is obtained in order to provide wide distribution throughout the diseased area.

It is known to use aqueous foams having a highly expanded volume. An example of such foam comprising prednisolone metasulphobenzoate is known from EP0774957. This patent teaches that an increased spreading of the active pharmaceutical along the intestine can be obtained by using a composition that exhibits a delayed foaming action. Such delayed foaming may be achieved by providing a composition in a pressurised container wherein the propellant is physically separated from said composition. However, the disadvantage of this single-dosage foaming composition is that although a highly expanded volume of the foam of up to 275 ml may be obtained, the initial volume of the unfoamed composition to be dosed is also extremely high (22 ml). Such high initial volume is disadvantageous since it requires the use of a large canister, especially when multiple doses are to be contained in said canister. The packaging and distribution of large canisters is an economic disadvantage. Furthermore, such large canister is very impractical to handle for the patient.

From the prior art compositions it appears that aerosol foams are complicated physical-chemical structures that do not form under arbitrary circumstances. In particular, a special balance between the foam-forming components is important. Slight shifts in the composition may already result in a collapse of the foam or alternatively the foam is not formed at all, especially when administration is to occur via an applicator nozzle with small diameter. Thus, a given formulation may not simply be adapted without further provisions to result in the desired foam. Especially, the problem with highly expandable foam-forming compositions according to the prior art is that due to their appearance preliminary ejection of said formed foam is easily induced. This results in insufficient retention of the active ingredient to the mucosa of the inflamed area which is necessary to obtain optimal results in combating the disease.

Hence, it is an object of the present invention to provide a foam-forming composition for prednisolone and its derivatives that solves the problems identified above.

Surprisingly, we have now found that an increased volume expansion ratio of the foam has a major effect on the appearance of the formed foam and hence provides an advantageous and clinically improved composition that may serve as an alternative for the few compositions that are currently available on the market.

DETAILED DESCRIPTION OF THE INVENTION

The present invention provides a foam-forming composition which exhibits a highly expanded foam volume and at the same time confers an appearance that allows sufficient contact time of the active to the target site in the intestine such as to obtain optimal local effect of the pharmaceutical active ingredient present in the foam.

Hence, in a first embodiment, it is provided an aqueous foam-forming composition suitable for rectal administration of a therapeutically effective amount of prednisolone or its pharmaceutically acceptable derivatives, characterized in that said composition has a volume expansion ratio in the range of 26 to 70. In a preferred embodiment of the present invention, the volume expansion ration is at least 26, preferably at least 28, more preferably at least 30. The volume expansion ratio is less than 70, more preferably less than 60, most preferably less than 50.

The volume expansion ratio (VER) is here defined as the ratio between the expanded volume of the foam ($V_f$ in ml) and the initial volume of the unfoamed starting material ($V_i$ in ml) according to the equation $VER=V_f/V_i$. The expanded volume of the foam ($V_f$) can be determined by emitting one dose of a predetermined volume or weight of unfoamed starting material in a vertical tube with radius (R) and subsequent measurement of the length (D) of the tube filled with the foam gives the volume of expansion according to the equation: $V_f=D\times\pi\times R^2$. The initial volume $V_i$ may be determined from the weight of the emitted dose divided by its density at 37° C. (generally, for aqueous compositions, the density is 1).

We have surprisingly found that by employing a foam-forming composition with increased volume expansion ratio, a foam is generated with an advantageous appearance, i.e. it collapses rather quickly but a thin layer of the components of the foam including the prednisolone remains on the surface of the intestine. This advantageous appearance allows for sufficient contact time between the active pharmaceutical ingredient and the mucous of the inflamed area, whereas a preliminary ejection reflex is at the same time minimised. Optimal uptake of the prednisolone from the foam into the inflamed mucous is hence established.

The composition of the present invention is an aqueous composition. For the present invention an aqueous composition means that a majority of the weight volume of the composition is composed of water, also referred to as the aqueous carrier. Preferably, the composition of the present invention comprises 57-97 weight percent of water, more preferably 65-95 weight percent. This aqueous carrier obviously also covers any aqueous buffer solution such as for example a phosphate buffer which apart from water also contain potassium phosphate and amounts of sodium hydroxide and hydrochloric acid to obtain the desired pH.

In a preferred embodiment of the present invention, said aqueous composition does not include emulsifying waxes and/or mineral oils. The disadvantage of these components is that they might further irritate the already inflamed areas of the intestine.

In yet another aspect, the composition of the present invention comprises at least one surfactant, a thickening agent and a propellant. Depending on the combination of surfactants and thickening agents, a person skilled in the art may first check the compatibility of said ingredients with the active ingredient. The thickening agent in the composition of the present invention may be chosen from any water-soluble polymer. Preferably, said thickening agent is a water-soluble cellulose polymer. Without being limiting, the following polymers may be included in the composition, e.g. carboxymethyl cellulose, polyoxyethylene-polyoxypropylene copolymers covered under the generic term poloxamer, xanthan gum, agar, guar gum, hydroxyethyl cellulose, hydroxypropyl cellulose, methyl cellulose. More preferably, hydroxypropyl methylcellulose is used. Typically, the weight percent of thickening agent is between 0.01 to 1% (w/w). In the present invention the amount is at most 1.0%, preferably at most 0.5%, more preferably it is at most 0.3% (w/w) of the composition. In the present invention, the minimum amount is at least 0.01%, preferably at least 0.05%, more preferably at least 0.1% (w/w) of the composition.

The precise identity of the surfactant present in the composition of the present invention is not critical and may be chosen from those which have an effective emulsifying action in combination with water and the foaming agent. Preferably, a mixture of two or more different surfactants is used. In said mixture at least one surfactant may provide the emulsifying action, whereas the other may provide a foam-stabilizing action. Known anionic and non-ionic surfactants may be used. In the composition of the present invention, the surfactant may be a mixture of at least two non-ionic surfactants since these are less irritating. Non-ionic surfactants may include glycerol fatty acid esters such as glycerol monostearate, glycol fatty acid esters such as propylene glycol monostearate, polyhydric alcohol fatty acid esters such as polyethylene glycol monooleate, polyoxyethylene fatty acid esters such as polyoxyethylene stearate, polyoxyethylene fatty alcohol ethers such as polyoxyethylene stearyl ether, polyoxyethylene sorbitan fatty acid esters such as polyoxyethylene sorbitan monooleate, sorbitan esters such as sorbitan monostearate, caprylocaproyl macrogolglycerides such as Labrasol®. Preferably, non-ionic surfactants that increase the viscosity of the foam-forming composition should be avoided. In a preferred embodiment, a mixture of caprylocaproyl macrogolglycerides and polyoxyethylene 80 sorbitan monooleate is used.

Suitably, the total amount of surfactant present in the composition makes up from 1% to 15% (w/w) of the composition, preferably it makes up less than 10% (w/w) of the total weight of the composition.

In a preferred embodiment of the present invention, the composition contains a lubricant. Preferably, said lubricant is silicone. In this preferred embodiment silicone further stabilizes the foam-forming composition. More preferably the silicone is polydimethylsiloxane. The amount of lubricant is at least 0.1%, preferably at least 0.5%, more preferably at least 1% (w/w) of the composition and at most 10%, preferably at most 5%, more preferably at most 3% (w/w) of the composition.

The propellant according to the present invention is used to accomplish the foaming effect. The propellant may be chosen according to known principles for preparing a foamable composition of the aerosol type packed in a pressurized container and suitable for a rectal application. The propellant may be any suitable gas such as a low molecular weight hydrocarbon e.g. isobutane, N-butane, propane, pentane, CFC, HFC, or air. Preferably, the propellant comprises a mixture of butane, isobutane, propane (B.I.P.). Suitably, the propellant may have a vapour pressure within the range of 0.5 to 2.5 bars (at ambient temperature). The propellant may be present in an amount from 4 to 12% (w/w) of the composition. Preferably, said amount is between 6 to 10%, more preferably between 7 to 9% (w/w) of the composition. Additionally, liquefied nitrogen may be present as pressurising agent to obtain the required number of doses. In a preferred embodiment, the pressure in a multi-dosage container is in the range of 5 to 12, more preferably 7 to 11 bars, and even more preferably 6 to 8 bars.

The composition of the present invention is suitable for rectal administration of a therapeutically effective amount of prednisolone or its pharmaceutically acceptable derivative. Particularly, the pharmaceutically acceptable derivative of prednisolone may be locally-acting forms of prednisolone. Preferably it is prednisolone metasulphobenzoate. The pharmaceutically acceptable salt is preferably a sodium salt. Suitably, in the foam-forming composition of the present invention also other locally-acting pharmaceutically active ingredients may be used. Preferably, they are selected from the group consisting of tixocortol pivalate, fluticasone propionate, beclomethasone dipropionate, mesalazine, budesonide and pharmaceutically acceptable salts of any of these.

The pharmaceutically active ingredient may be present in any effective amount that causes a therapeutically effect in the patient. The pharmaceutically active ingredient is preferably present in amounts of approximately 0.005% by weight to approximately 10% by weight, more preferably approximately 0.05% to approximately 2% by weight, based on the total weight of the foam-forming composition.

The foam-forming composition may also contain other ingredients such as preservatives, lubricants and chelating agents. Typical preservatives include sodium benzoate, sorbic acid, phenylethylic alcohol and parahydroxybenzoate. The chelating agent may include EDTA.

In yet another embodiment of the present invention a multi-dose pressurized aerosol container is provided that comprises the foam-forming composition according to the invention. The problem with foam-forming compositions comprised in a multi-dose aerosol container is the insufficient dose-repeatability of the emitted foam. It appears that the amount of active present in a single dose and the expansion volume of an emitted dose may fluctuate between the first and last dose in a range that is outside the target range. Since it is prerequisite for the development of an advantageous multi-dose rectal formulation that all given doses are within the specified narrow range with regard to both the amount of the active and the reached end-volume of the dose, such high dose-repeatability is critical for developing a commercially advantageous product.

We have now surprisingly found that by employing a low viscosity of the foam-forming composition, it is possible to produce foam with sufficient dose-repeatability.

Although aqueous foaming compositions with both low and high viscosities have been described in EP 0735860 for mesalazine, this document does not teach that viscosity of the foam-forming composition positively influences the dose-repeatability of the foam.

The composition of the present invention preferably has a viscosity in the range of 2.0 to 20.0 mPa·s. The viscosity of the composition is at least 2.0 mPa·s, preferably it is at least 4.0 mPa·s, more preferable at least 6.0 mPa·s and most preferable at least 7.0 mPa·s. The viscosity of said composition is maximal 20.0 mPa·s, preferably it is less than 16.0 mPa·s, more preferably less than 12.0 mPa·s and most preferably less than 9.0 mPa·s.

For the present invention, with viscosity of the foam-forming composition is meant the viscosity of the unfoamed composition comprising all components making up the foam-forming composition except the foaming agent(s). The viscosity of the emulsion can be determined using any suitable viscosimeter operated according to standard procedures. For the present invention, viscosities were measured by means of a Brookfield RVT with a cone plate CP 42 mobile for which the rotation speed of the emulsion during measurement is corrected with a standard coefficient. For the present invention, the viscosity (in cP or mPa·s) is determined at 25° C. and 100 rpm.

In yet another embodiment, the multi-dose container comprises a metering valve. Metering valves are valves that dispense a predetermined and constant dose of foam. Suitably, a metering valve adapted to dispense volumes of from approximately 1 to 5 cm³ may be used (provided by Lablabo, France). The container may be a coated aluminum canister. Further, the container can be fitted or supplied together with an application device for insertion into the rectum to ensure more efficient administration of the foam.

In yet another aspect of the present invention, a method for preparation of the foam-forming composition is provided. The foam-forming composition according to the present invention is prepared according to a method comprising the steps of admixing an aqueous carrier, a lubricant, a thickening agent, at least one surfactant and the pharmaceutically active ingredient to form a homogenous bulk emulsion. Preferably, said method comprises the steps of
a) Admixing an aqueous carrier, a lubricant, at least one surfactant and a locally-acting pharmaceutically active ingredient or its pharmaceutically acceptable derivative to obtain a homogenous emulsion having a viscosity in the range of 2 to 20 mPa·s; and
b) Adding to the emulsion obtained in step a) at least one propellant to form a foam-forming composition.

Typically, the preservatives and chelating agents are first admixed with the aqueous carrier by means of a homogenizer. Then, the thickening agent is admixed in the same way. Subsequently, the surfactant(s) and lubricant are admixed and the mixture may be solubilized and/or heated before the active ingredient is added. Alternatively, the active ingredient is admixed at the start.

Canisters may be filled with the bulk emulsion and subsequently after sealing, a propellant is added to form the foam-forming composition.

The foam-forming composition according to the present invention will usually be packed in a suitable pressurized dispensing canister of the aerosol type well known in the art such as an aluminum canister. Each canister is sealed with a suitable foam dispensing valve. Any valve or nozzle/valve assembly which provides a means for releasing the foam-forming emulsion from the container and provides a foam is suitable for use in the present invention.

The foam that is formed from the composition of the present invention has superior properties. The advantages associated with the highly expanded foam according to the present invention is that better results are obtained in combating the disease and either a lower dosage of the active ingredient or less dosages per day are necessary to obtain similar results when compared with prior art compositions. For instance, in patients that are using the composition of the present invention, the likelihood of inducing a defecation or rejection reflex on administration of said foam is lower than normally may be expected from foam having a high expansion volume. Further, the increased spreading of the foam together with the longer exposure time to the active will result in optimal local effect at the target site. Also, the foam of the present invention does not cause extra irritation of the inflamed target mucosa due to the absence of emulsifying waxes and/or technical oils as present in the prior art compositions. Due to these superior properties of the foam, the current invention represents a valuable alternative to previously known medicines used for the treatment of rectal diseases.

The present invention is further illustrated by the following examples which should not be interpreted as limiting the scope of the invention.

EXAMPLE 1

Preparation of the Bulk Emulsion

A pharmaceutical foam-forming composition was formulated with prednisolone sodium metasulphobenzoate as active ingredient according to the formula shown in Table I.

TABLE I

Composition of the bulk emulsion

| Composition of the product | Function | Quantity (g) |
| --- | --- | --- |
| Active Pharmaceutical Ingredient: | | |
| Prednisolone sodium metasulphobenzoate | Active pharmaceutical ingredient | 1.19 |
| Other components: | | |
| Sorbic acid | Preservative | 0.045 |
| Phenyl ethyl alcohol | Preservative | 0.225 |
| Edetic acid (disodium salt) | Preservative | 0.009 |
| METOLOSE ® 90SH 15000 Hydroxypropyl Methylcellulose | Thickening agent | 0.135 |
| MONTANOX ® 80 VG PHA Polysorbate 80 | Emulsifying agent | 4.158 |
| LABRASOL ® caprylocaproyl macrogolglycerides | Emulsifying agent | 4.158 |
| DOW CORNING ® Q7-9120 silicone fluid Polydimethylsiloxane | Lubricant | 1.350 |
| Purified Water | Solvent | 78.73 |

The bulk emulsion is prepared by introducing the Sorbic acid (E200), Phenylethyl alcohol (CAS 60-12-8) and Edetic acid (CAS 6381-92-6) into the water carrier while mixing in a Chabaud® mixer during 10 minutes at 1500 rpm. Subsequently the hydroxypropyl methylcellulose was added under quick stirring at 3000 rpm during 10 minutes, and further stirring for 60 minutes at 1000 rpm. Following, the polysorbate 80 (Montanox®, Seppic S.A.), the caprylocaproyl macrogolglycerides (Labrasol®, Gattefosse Corporation) and polydimethylsiloxane (Dow Corning® Q7-9120 silicone fluid, 100 CST, 425G, Dow Corning) was added under stirring for 15 minutes at 1500 rpm. Finally, Prednisolone meta-sulphobenzoate sodium salt (CAS 630-67-1) was incorporated into the emulsion under quick stirring at 3000 rpm during 15 minutes. The formed homogenous emulsion has a pH of 4.15. Viscosity was measured using a Brookfield viscometer (RTV mobile with Cone and plate CP 42). This viscometer is a torque meter which is driven at discrete rotational speeds. The amount of torque that is indicated must be converted to absolute centipoise units (cP) or mPa·s from pre-calculated range charts (Brookfield). The viscosity measured at 25° C. and 100 rpm was 7.6 mPa·s.

EXAMPLE 2

Preparation of the Foam-Forming Composition

A monoblock canister (110 ml) was filled with 90 gram of the bulk emulsion according to experiment 1, and further filled with the propellants B.I.P. (Novospray nbu/p25 of Avantec-dehon; 8.110 g) and as pressurizing agent Nitrogen (0.09 g) is added using a pressurisation unit and resulting in a pressure of 12 bars. The canister was closed with a 3 ml metering valve (Lablabo S.A.). The canister contains material for 14 dosages (and 20% overdoses) and the repeatability of the dose and the expansion volume was established by measuring respectively the volumic mass (g/ml) and the expansions volume (ml) of the $1^{st}$ and the $14^{th}$ dose (Table II).

TABLE II

| Characteristics of the foam | | |
|---|---|---|
| | Dose number 1 | Dose number 14 |
| Expansion volume (ml) (n = 5) | 90.60 (SD 3.76) | 90.00 (SD 1.22) |
| Volumic mass (g/ml) (n = 5) | 0.031 (SD $1.3 \times 10^{-3}$) | 0.030 (SD $3.2 \times 10^{-3}$) |

SD: standard deviation

Expansion volume was determined by emitting a single dose (3 ml) into the down extremity of a plastic tube that stand in a vertical position having an internal diameter (I.D) of 1.2 cm and a length of 100 cm and having a scale indication in centimetres. The maximum length of the tube filled with foam volume is recorded (D) and subsequently, the volume of expansion is calculated by the equation $V_{exp}=D \times \pi \times r^2$ wherein r is the radius of the tube (i.e. 0.6 cm). The volume expansion ratio was found to be 30.

The volumic mass (g/ml) of a single dose is calculated by dividing the weight of the dose (g) by the expansion volume (ml). The weight of the dose is determined by measuring on a balance (Mettler PR 802, 0.01 mg precision) the difference in weight of the canister before and after emitting said dose.

The invention claimed is:

1. An aqueous foam-forming composition for rectal administration of a therapeutically effective amount of prednisolone or its pharmaceutically acceptable derivatives, said composition comprising 1-15% (w/w) of surfactant, 0.01-1% (w/w) of thickening agent, 0.1-10% (w/w) of a silicone lubricant, 4-12% (w/w) of propellant, wherein said composition has a volume expansion ratio of at least 26 and a viscosity in the range of 2.0 to 20.0 mPa.

2. The composition according to claim 1, wherein the volume expansion ratio is at least 28.

3. The composition according to claim 1, wherein the volume expansion ratio is between 26 and 70.

4. The composition according to claim 1, where the pharmaceutically acceptable derivative of prednisolone is a salt.

5. The composition according to claim 1, wherein the thickening agent is a water soluble cellulose polymer, wherein the water soluble cellulose polymer is between 0.01% and 1.0% (w/w) of the composition.

6. The composition according to claim 1, wherein the surfactant is a mixture of at least two non-ionic surfactants.

7. The composition according to claim 1, wherein the propellant comprises a mixture of butane, isobutane, propane (B.I.P.) in an amount of 4 to 12% (w/w) of the composition.

8. A multi-dose pressurized aerosol container comprising the foam-forming composition according to claim 1.

9. The multi-dose container according to claim 8, wherein the viscosity of the foam-forming composition is in the range of 2.0 to 20.0 mPa.

10. The multi-dose container according to claim 8, comprising a metering valve.

11. A method for preparing a foam-forming composition according to claim 1, comprising the steps of
   a) admixing an aqueous carrier, a lubricant, at least one surfactant and a locally-acting pharmaceutically active ingredient or its pharmaceutically acceptable derivative to obtain a homogenous emulsion having a viscosity in the range of 2 to 20 mPa; and
   b) adding to the emulsion obtained in step a) at least one propellant to form a foam-forming composition.

12. The composition according to claim 2, wherein the volume expansion ratio is at least 30.

13. The composition according to claim 1, wherein the volume expansion ratio is between 26 and 60.

14. The composition according to claim 1, wherein the volume expansion ratio is between 26 and 50.

15. The composition according to claim 5, wherein the thickening agent is between 0.05% and 0.5% (w/w) of the composition.

16. The composition according to claim 5, wherein the thickening agent is between 0.1% and 0.3% (w/w) of the composition.

17. The composition according to claim 7, wherein the mixture of butane, isobutane, propane (B.I.P.) is between 6 and 10% (w/w) of the composition.

18. The composition according to claim 7, wherein the mixture of butane, isobutane, propane (B.I.P.) is between 7 and 9% (w/w) of the composition.

19. The composition according to claim 1, wherein the surfactant is selected from the group consisting of glycerol monostearate, propylene glycol monostearate, polyethylene glycol monooleate, polyoxyethylene stearate, polyoxyethylene stearyl ether, polyoxyethylene sorbitan monooleate, sorbitan monostearate, caprylocaproyl macrogolglycerides (Labrasol®), polyoxyethylene 80 sorbitan monooleate (Polysorbate 80), and mixtures thereof.

20. The composition according to claim 1, wherein the surfactant is a mixture of polyoxyethylene 80 sorbitan monooleate (Polysorbate 80) and caprylocaproyl macrogolglyceride (Labrasol®).

21. The composition according to claim 1, wherein the thickening agent is selected from the group consisting of carboxymethyl cellulose, polyoxyethylene-polyoxypropylene copolymer, xanthan gum, agar, guar gum, hydroxyethyl cellulose, hydroxypropyl cellulose, methyl cellulose, hydroxypropyl methylcellulose, and mixtures thereof.

22. The composition according to claim 1, wherein the thickening agent is hydroxypropyl methylcellulose.

23. The composition according to claim 1, wherein the propellant is selected from the group consisting of butane, isobutane, propane, pentane, CFC, HFC, air, and mixtures thereof.

\* \* \* \* \*

UNITED STATES PATENT AND TRADEMARK OFFICE
CERTIFICATE OF CORRECTION

PATENT NO. : 8,206,688 B2
APPLICATION NO. : 12/161102
DATED : June 26, 2012
INVENTOR(S) : Francois Jean-Louis Jerome Boutignon et al.

Page 1 of 1

It is certified that error appears in the above-identified patent and that said Letters Patent is hereby corrected as shown below:

In claims 1, 9 and 11 of the printed patent, column 8, line numbers 10, 31 and 41, please change "mPa" to --mPa.s--

Signed and Sealed this
Twenty-fifth Day of September, 2012

David J. Kappos
*Director of the United States Patent and Trademark Office*